(12) United States Patent
Marcuccio et al.

(10) Patent No.: US 6,448,433 B1
(45) Date of Patent: Sep. 10, 2002

(54) PROCESS FOR PREPARING ORGANIC BORONIC ACID DERIVATIVES USING DIBORONIC ACID

(75) Inventors: Sebastian Mario Marcuccio, Endeavour Hills; Mary Rodopoulos, Blackburn South; Helmut Weigold, Mount Waverley, all of (AU)

(73) Assignee: Commonwealth Scientific and Industrial Research Organization, Campbell (AU)

( * ) Notice: Subject to any disclaimer, the term of this patent is extended or adjusted under 35 U.S.C. 154(b) by 0 days.

(21) Appl. No.: 09/486,696

(22) PCT Filed: Sep. 8, 1998

(86) PCT No.: PCT/AU98/00726

§ 371 (c)(1),
(2), (4) Date: May 10, 2000

(87) PCT Pub. No.: WO99/12940

PCT Pub. Date: Mar. 18, 1999

(30) Foreign Application Priority Data

Sep. 8, 1997 (AU) .............................. PO 9038

(51) Int. Cl.$^7$ ................................................... C07F 5/02
(52) U.S. Cl. .......................................................... 562/7
(58) Field of Search ............................................. 562/7

(56) References Cited

PUBLICATIONS

CA:117:8626 abs of Makromol. Chem by Kallitsis et al 193(4) pp. 1021–1029, 1992.*

Tetrahedron Letters, vol. 38, No. 38, 1997, M.H. Todd et al., "Studies on the Synthesis, Characterisation and Reactivity of Aromatic Diboronic Acids".

Organic Preparations and Procedures International, vol. 23, No. 6, 1991, K. Ramalingam and D.P. Nowotnik, "Syntheses of Some Isothiocyanatophenylboronic Acids".

* cited by examiner

Primary Examiner—Jean F. Vollano
(74) Attorney, Agent, or Firm—Bacon & Thomas

(57) ABSTRACT

The invention relates to a process for the preparation of organic boronic acid derivatives involving the reaction of an organic compound with diboronic acid in the presence of a Group 8–11 metal catalyst.

12 Claims, No Drawings

PROCESS FOR PREPARING ORGANIC BORONIC ACID DERIVATIVES USING DIBORONIC ACID

This application is the national stage of PCT/AU98/00726, filed Sep. 8, 1998, now WO 99/12940.

The present invention relates to a method for preparing boron derivatives of organic compounds, in particular to boronic acid derivatives of organic compounds.

Boronic acid derivatives of organic compounds are of particular interest, not only as intermediary means for forming covalent carbon-carbon bonds between organic compounds, but as a starting point for further chemical manipulations and transformations or in conferring or increasing biological activity to otherwise biologically inactive compounds.

Whilst these boronic acid derivatives may be obtained by conventional hydrolysis or hydrogenolysis procedures applied to boronic ester compounds, many conventional conditions employed in the preparation of boronic ester compounds are incompatible with compounds bearing sensitive functionalities. Furthermore, there are practical and commercial advantages in reducing the number of chemical manipulations employed in a synthetic procedure and it is therefore desirable to obtain the boronic acid derivatives directly.

It has now surprisingly been found that diboronic acid can be reacted in the presence of a Group 8–11 metal catalyst with an organic compound under mild conditions to provide boronic acid derivatives directly, thereby circumventing the hydrolysis or hydrogenolysis step and allowing for the presence of sensitive functional groups.

Accordingly, the present invention provides the use of diboronic acid in the preparation of organic boronic acid derivatives containing at least one boronic acid residue.

The invention further provides a process for preparing organic boronic acid derivatives comprising reacting an organic compound having a boron reactive site with diboronic acid in the presence of a Group 8–11 metal catalyst.

The use of diboronic acid offers a convenient and advantageous means of introducing a boronic acid residue into an organic compound over conventional reagents. Its stability towards water and oxygen under ambient conditions provides for ease of use when compared with other reactive and sensitive reagents used to make boronic acids via the esters, which require a strictly controlled environment.

In the preparation of organic boronic acids, the use of diboronic acid affords a number of advantages over that of diboronic acid esters. Firstly, diboronic acid itself is readily prepared from tetra(dimethylamino)diboron. Secondly, the need for a hydrolysis or hydrogenolysis step is circumvented as the boronic acid is the primary reaction product. Thirdly, by avoiding a hydrolysis or hydrogenolysis step, the formation of alcoholic by-products in the reaction mixture is eliminated.

Diboronic acid can be dehydrated (T Wartik and E. F. Apple *J Am. Chem. Soc.* 1955 77 6400; 1958 80 6155).

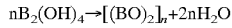

It has now been found that the dehydrated form of diboronic acid can also be used to prepare boronic acid derivatives. The boron to boron bond of the dehydrated form is stable in refluxing methanol, ethanol, isopropyl alcohol or t-butyl alcohol and is not cleaved by cold water. The dehydrated form is soluble in methanol at room temperature, dissolves rapidly in ethanol or isopropanol on warning, and in t-butyl alcohol at 82° C. (A. L. McClosky, R. J. Brotherton & J. L. Boone, *J Am Chem. Soc.* 1961 83 4750)

As used herein, the term "diboronic acid or tetrahydroxydiboron" refers to $(HO)_2B—B(OH)_2$ or its dehydration product; and the term "boronic acid residue" refers to the group $—B(OH)_2$.

The term "organic boronic acid derivative" refers to an organic compound having a boronic acid residue at a substitution position.

The term "boron reactive site" as used herein refers to any carbon atom within a molecule capable of reacting with diboronic acid in the presence of a Group 8–11 metal catalyst to provide a boronic acid residue on that carbon atom. Examples of boron reactive sites include carbon atoms having halogen or halogen-like substituents, carbon atoms taking part in carbon to carbon double or triple bonds, and carbon atoms in an allylic position having a substituent leaving group.

It has been found, in particular, that when an organic compound having a halogen or halogen-like substituent is reacted with diboronic acid in the presence of a Group 8–11 metal catalyst and a suitable base, the halogen or halogen-like substituent on the organic compound can be replaced by a boronic acid residue.

Accordingly, in one embodiment of the invention, there is provided a process for preparing organic boronic acid derivatives which comprises reacting an organic compound having a halogen or halogen-like substituent at a substitution position with diboronic acid in the presence of a Group 8–11 metal catalyst and a suitable base such that the halogen or halogen-like substituent is substituted with a boronic acid residue.

As used herein, the term "organic compound having a halogen or halogen-like substituent at a substitution position" refers to any organic compound having a carbon to halogen or carbon to halogen-like substituent bond at a position at which substitution by a boronic acid residue is desired. The organic compound may be aliphatic, olefinic, acetylenic, aromatic, polymeric, dendritic, cyclic or any combination thereof. The compound may further comprise additional heteroatoms such as sulfur, oxygen, nitrogen, phosphorous, boron, silicon, arsenic, selenium, and tellurium.

The terms "aromatic" and "aromatic compound(s)" as used herein refer to any compound which includes or consists of one or more aromatic rings. The aromatic rings may be carbocyclic, or heterocyclic, and may be mono or polycyclic ring systems. Examples of suitable rings include but are not limited to benzene, biphenyl, terphenyl, quaterphenyl, naphthalene, tetradyronaphthalene, 1-benzylnaphthalene, anthracene, dihydroanthracene, benzanthracene, dibenzanthracene, phenanthracene, perylene, pyridine, 4-phenylpyridine, 3-phenylpyridine, thiophene, benzothiophene, naphthothiophene, thianthrene, furan, pyrene, isobenzofuram, chromene, xanthene, phenoxathiin, pyrrole, imidazole, pyrazole, pyrazine, pyrimidine, pyridazine, indole, indolizine, isoindole, purine, quinoline, isoquinoline, phthalazine, quinoxaline, quinazoline, quinoline, pteridine, carbazole, carboline, phenanthridine, acridine, phenanthroline, phenazine, isothiazole, isooxazole, phenoxazine and the like, each of which may be optionally substituted. The terms "aromatic" and "aromatic compound(s)" include molecules, and macromolecules, such as polymers, copolymers and dendrimers which include or consist of one or more aromatic rings. The term "pseudoaromatic" refers to a ring system which is not strictly aromatic, but which is stabilized by means of delocalization of π electrons and behaves in a similar manner to aromatic rings. Examples of pseudoaromatic rings include but are not limited to furan, thiophene, pyrrole and the like.

The term "olefinic compound" and "olefinic organic compound" as used herein refers to any organic compound having at least one carbon to carbon double bond which is not part of an aromatic or pseudo aromatic system. The olefinic compounds may be selected from optionally substituted straight chain, branched or cyclic alkenes; and molecules, monomers and macromolecules such as polymers and dendrimers, which include at least one carbon to carbon double bond. Examples of suitable olefinic compounds include but are not limited to ethylene, propylene, but-1-ene, but-2-ene, pent-1-ene, pent-2-ene, cyclopentene, 1-methylpent-2-ene, hex-1-ene, hex-2-ene, hex-3-ene, cyclohexene, hept-1-ene, hept-2-ene, hept-3-ene, oct-1-ene, oct-2-ene, cyclooctene, non-1-ene, non-4-ene, dec-1-ene, dec-3-ene, buta-1,3-diene, penta-1,4-diene, cyclopenta-1,4-diene, hex-1,4, diene, cyclohexa-1,3-diene, cyclohexa-1,4-diene, cyclohepta-1,3-diene, cyclohepta-1,3,5-triene and cycloocta-1,3,5,7-tetraene, each of which may be optionally substituted. Preferably the straight chain, branched or cyclic alkene contains between 1 and 20 carbon atoms.

The olefinic compounds may be α,β-unsaturated carbonyl compounds, or conjugated dienes. The term "conjugated dienes" as used herein refers to any compound capable of acting as a diene in a Diels-Alder reaction. The olefinic compound may also be an organic compound having a leaving group in an allylic position.

The term "acetylenic compound" as used herein refers to any compound having at least one carbon to carbon triple bond. The acetylenic compounds may be selected from optionally substituted straight chain, branched or cyclic alkynes and molecules, monomers and macromolecules such as polymers and dendrimers, which include at least one carbon to carbon triple bond. Examples of suitable acetylene compounds include, but are not limited to acetylene, propyne, but-1-yne, but-2-yne, pent-1-yne, pent-2-yne, hex-1-yne, hex-2-yne, hex-3-yne, cyclohexyne, hep-1-yne, hept-2-yne, hept-3-yne, cycloheptyne, oct-1-yne, oct-2-yne, oct-3-yne, oct-4-yne, cyclooctyne, nonyne, decyne, 1,3,5-trioctyne, 2,4-dihexyne, each of which may be optionally substituted. Preferably the straight chain, branched or cyclic alkyne contains between 1 and 20 carbon atoms.

The term "substitution position" as used herein refers to a position on an organic compound at which substitution with a boronic acid residue is desired. Each organic compound may have one or more, preferably between 1 and 6, substitution positions. In an aromatic compound it is preferred that the substitution position is directly on the ring and with an olefinic compound it is preferred that the substitution position is at a vinylic position. If the organic compound is a polymer or a dendrimer it may have many substitution positions.

In this specification "optionally substituted" means that a group may or may not be substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, isocyano, cyano, formyl, carboxyl, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, imino, alkylimine, alkenylimine, alkynylimino, arylimino, benzylimino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy mercapto, alkylthio, benzylthio, acylthio, sulphonamido, sulfanyl, sulfo and phosphorus-containing groups.

In one aspect of this invention, the organic compound must include at least one halogen or halogen-like substituent at a substitution position to enable reaction with the diboronic acid. The terms "halogen-like substituent" and "pseudo-halide" refer to any substituent which, if present on an organic compound, may react with diboronic acid in the presence of a palladium catalyst and base to give an organic boronic acid derivative. Preferred halogen substituents include I, Br and Cl. The reactivity of chloro substituted aromatic ring compounds can be increased by selection of appropriate ligands on the palladium catalyst. Examples of halogen-like substituents include triflates and mesylates, diazonium salts, phosphates and those described in Palladium Reagents & Catalysts (Innovations in Organic Synthesis by J. Tsuji, John Wiley & Sons, 1995, ISBN 0-471-95483-7).

As used herein, the term "leaving group" refers to a chemical group which is capable of being displaced by a boronic acid residue. Suitable leaving groups are apparent to those skilled in the art and include halogen and halogen-like substituents, as well as ester groups.

The process according to the present invention is especially suitable for the preparation of organic boronic acid derivatives which contain substituents which are reactive with organometallic compounds, such as Grignard reagents or alkyl lithiums, therefore unsuitable for reacting using standard Grignard methodology unless these substituents are first protected. One such class of reactive substituents are the active hydrogen containing substituents. The term "active hydrogen containing substituent" as used herein refers to a substituent which contains a reactive hydrogen atom. Examples of such substituents include but are not limited to hydroxy, amino, imino, acetyleno, carboxy (including carboxylato), carbamoyl, carboximidyl, sulfo, sulfinyl, sulfinimidyl, sulfinohydroximyl, sulfonimidyl, sulfondiimidyl, sulfonohydroximyl, sultamyl, phosphinyl, phosphinimidyl, phosphonyl, dihydroxyphosphanyl, hydroxyphosphanyl, phosphono (including phosphonato), hydrohydroxyphosphoryl, allophanyl, guanidino, hydantoyl, ureido, and ureylene. Of these substituents it is particularly surprising that the reaction can be conducted with hydroxy and amino substituents in view of their high reactivity. Carboxyl, sulfo and the like (i.e. acidic) substituents may require additional base. Other reactive substituents include trimethylsilyl.

In the above definitions, the term "alkyl", used either alone or in compound words such as "alkenyloxyalkyl", "alkylthio", "alkylamino" and "dialkylamino" denotes straight chain, branched or cyclic alkyl, preferably $C_{1-20}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2-, or 3-propylhexyl, decyl, 1-, 2-, 3-, 4-, 5-, 6-, 7- and 8-methylnonyl, 1-, 2-, 3-, 4-, 5-, or 6-ethyloctyl, 1-, 2-, 3- or 4-propylheptyl, undecyl, 1-, 2-, 3-, 4-, 5-, 6-,7,8- or 9-methyldecyl, 1-, 2-, 3-, 4-, 5-, 6- or 7-ethylnonyl, 1-, 2-, 3-, 4- or 5-prppylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

The term "alkoxy" denotes straight chain or branched alkoxy, preferably $C_{1-20}$ alkoxy. Examples of alkoxy include methoxy, ethoxy, n-propoxy, isopropoxy and the different butoxy isomers.

The term "alkenyl" denotes groups formed from straight chain, branched or cyclic alkenes including ethylenically mono-, di- or poly-unsaturated alkyl or cycloalkyl groups as previously defined, preferably $C_{2-20}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4, pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

The term "alkynyl" denotes groups formed from straight chain, branched or cyclic alkyne including alkyl and cycloalkyl groups as previously defined which contain a triple bond, preferably $C_{2-20}$ alkynyl. Examples of alkynyl include ethynyl, 2,3-propynyl and 2,3- or 3,4-butynyl.

The term "acyl"either alone or in compound words such as "acyloxy", "acylthio", "acylamino" or "diacylamino" denotes carbamoyl, aliphatic acyl group and acyl group containing an aromatic ring which is referred to as aromatic acyl, or a heterocyclic ring which is referred to as heterocyclic acyl, preferably $C_{1-20}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxyearbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

The terms "heterocyclic", "heterocyclyl" and "heterocycl" as used herein on their own or as part of a group such as "heterocyclicalkenoyl", heterocycloxy" or "haloheterocyclyl" refer to aromatic, pseudo-aromatic and non-aromatic rings or ring systems which contain one or more heteroatoms selected from N, S, O and P and which may be optionally substituted. Preferably the rings or ring systems have 3 to 20 carbon atoms. The rings or ring systems may be selected from those described above in relation to the definition of "aromatic compound(s)".

The term "aryl" as used herein on its own or as part of a group such as "haloaryl" and "aryloxycarbonyl" refers to aromatic and pseudo-aromatic rings or ring systems composed of carbon atoms, preferably between 3 and 20 carbon atoms. The rings or ring systems may be optionally substituted and may be selected from those described above in relation to the definition of "aromatic compound(s)".

It has also been found that in the presence of a Group 8–11 metal catalyst, diboronic acid may add across a carbon to carbon double or triple bond of an olefinic or acetylenic compound such that a boronic acid residue is introduced on each of the carbon atoms of the respective double or triple bond, such that the double bond becomes a single bond and the triple bond becomes a double bond. In the case of two or more conjugated double bonds the boronic acid residues may be introduced on the distal carbon atoms participating in the conjugation resulting in loss of conjugation. In the case of an α,β-unsaturated carbonyl compound, a single boronic acid residue is introduced on the β-carbon and the α,β-unsaturation is lost.

The term "distal" as used herein in relation to carbon atoms participating in conjugation refers to the carbon atoms at each end of the conjugated chain of carbon atoms. For example, the distal carbon atoms in 1,3-butadiene are carbon atoms 1 and 4.

The expression "loss of conjugation" as used herein refers to the conversion of a double bond of a conjugated system into a single bond. This may result in complete loss of conjugation or partial loss of conjugation. In some cases there may be some rearrangement following loss of conjugation.

Accordingly, in another embodiment of the invention, there is provided a process for preparing organic boronic acid derivatives which comprises reacting an olefinic organic compound having at least one carbon to carbon double bond or an acetylenic compound having at least one carbon to carbon triple bond, with diboronic acid in the presence of a Group 8–11 metal catalyst such that a boronic acid residue is introduced on one or two of the carbon atoms of the respective double or triple bond.

The term "Group 8–11 metal catalyst" as used herein refers to a catalyst comprising a metal of Groups 8–11 of the periodic table described in *Chemical and Engineering News*, 63(5), 27, 1985.

Examples of Group 8–11 metal catalysts include platinum metal, Pt(O) complexes analogous to the palladium complexes described in detail below, or complexes readily reduceable to the Pt(O) state. Other examples include iron, cobalt, nickel, copper, ruthenium, rhodium, palladium, silver, osmium, iridium, platinum, gold and analogous complexes of these metals. Metals and complexes with readily accessible low oxidative states are particularly suitable. Preferred catalysts are those that readily under oxidative addition and reductive elimination. One skilled in the art would readily be able to select a suitable catalyst on this basis.

When the Group 8–11 metal catalyst is a palladium catalyst it may be a palladium complex. Examples of suitable palladium catalysts include but are not limited to $PdCl_2$, $Pd(OAc)_2$, $PdCl_2(dppf)CH_2Cl_2$, $Pd(PPh_3)_4$ and related catalysts which are complexes of phosphine ligands, (such as $(Ph_2P(CH_2)_nPPh_2)$ where n is 2 to 4, $P(o-tolyl)_3$, $P(i-Pr)_3$, $P(cyclohexyl)_3$, $P(o-MeOPh)_3$, $P(p-MeOPh)_3$, dppp, dppb, TDMPP, TTMPP, TMPP, TMSPP and related water soluble phosphines), related ligands (such as triarylarsine, triarylantimony, triarylbismuth), phosphite ligands (such as $P(OEt)_3$, $P(O-p-tolyl)_3$, $P(O-o-tolyl)_3$ and $P(O-iPr)_3$) and other suitable ligands including those containing P and/or N atoms for coordinating to the palladium atoms, (such as for example pyridine, alkyl and aryl substituted pyridines, 2,2'-bipyridyl, alkyl substituted 2,2'-bipyridyl and bulky secondary or tertiary amines), and other simple palladium salts either in the presence or absence of ligands. The palladium catalysts include palladium and palladium complexes supported or tethered on solid supports, such as palladium on carbon, as well as palladium black, palladium clusters, palladium clusters containing other metals, and palladium in porous glass as described in J. Li, A. W-H. Mau and C. R. Strauss, Chemical Communications, 1997, p1275. The same or different palladium catalysts may be used to catalyse different steps in the process. The palladium catalyst may also be selected from those described in U.S. Pat. No. 5,686,608. In certain reactions there are advantages in using ligands with altered basicity and/or steric bulk.

Preferred catalysts are palladium and platinum catalysts as described above. Where the reacting involves an organic compound having a halogen or halogen-like substituent palladium catalysts are especially preferred. Where the organic compound is olefinic or acetylenic platinum catalysts are especially preferred.

It has also been found that when an organic compound containing a carbon to carbon double bond and a leaving group at an allylic position, is reacted with diboronic acid in the presence of a Group 8–11 metal catalyst, the leaving group can be replaced by a boronic acid residue. Preferably the leaving group is an ester group.

Accordingly, in yet another embodiment, there is provided a process for preparing organic boronic acid derivatives which comprises reacting an olefinic compound having a leaving group at an allylic substitution position with diboronic acid in the presence of a Group 8–11 metal catalyst such that the leaving group is replaced with a boronic acid residue.

This reaction may be performed in the presence of a suitable base.

The process may be performed in any suitable solvent or solvent mixture. Examples of such solvents include amides of the lower aliphatic carboxylic acids and lower aliphatic secondary amines, DMSO, aromatic hydrocarbons, nitromethane, acetonitrile, benzonitrile, ethers, polyethers, cyclic ethers, lower aromatic ethers, lower alcohols, and their esters with the lower aliphatic carboxylic acids, pyridine, alkylpyridines, cyclic and the lower secondary and tertiary amines, and mixtures thereof, including mixtures with other solvents.

In a preferred embodiment of the invention the process is performed in a protic solvent. Examples of suitable protic solvents include water and lower alcohols. Most preferably the solvent is water, ethanol, methanol, isopropanol or mixtures thereof, including mixtures with other solvents.

The temperature at which each step of the process according to the invention is conducted will depend on a number of factors including the desired rate of reaction, solubility and reactivity of the reactants in the selected solvent, boiling point of the solvent, etc. The temperature of the reaction will generally be in the range of –100 to 250° C. In a preferred embodiment the process is performed at a temperature between –20 and 80°, more preferably between 15 and 40° C.

The term "suitable base" as used herein refers to a basic compound which. when present in the reaction mixture, is capable of catalysing, promoting or assisting reaction between reactants. The base may be suitable for catalysing a single step, or more than one step, depending on the desired outcome of the reaction. For example a base may be chosen which catalyses reaction between the organic compound and the diboronic acid, but which is strong enough to catalyse further reaction of organic diboronic acid derivative with additional organic compound or to other organic compounds. It is also preferable that a base is chosen which is soluble in the solvent to which it is added. Examples of bases which are suitable for catalysing the reaction of the organic compound with the diboronic acid include, carboxylates (for example potassium acetate), fluorides, hydroxides, cyanides and carbonates of Li, Na, K, Rb, Cs, ammonium and the group 2 metals Mg, Ca, & Ba, the alkali metal (Li, Na, K, Rb, Cs) phosphates and the phosphate esters (eg. $C_6H_5OP(O)(ONa)_2$ and related aryl and alkyl compounds) and their alkoxides and phenoxides, thallium hydroxide, alkylammonium hydroxides and fluorides. Some of these bases may be used in conjunction with a phase transfer reagent, such as for example tetraalkylammonium salts or the crown ethers.

It is possible to use stronger bases, such as $K_2CO_3$, for catalysing the reaction of an organic compound having a halogen or halogen-like substituent at a substitution position with the diboronic acid by using lower reaction temperatures, for example –20° C. to 25° C. When coupled product is required this can be achieved by selection of an appropriate temperature. The appropriate temperature will depend on the particular solvent, base and organic compound utilised. It is also possible to control the reaction conditions to form symmetrical coupled products using a strong base. In some cases it may be necessary to raise the temperature of the reaction medium to allow the coupling reaction to proceed. The use of a single base to perform the substitution stage and the coupling step provides a very convenient route to a large range of coupled products.

The term "vinylic substitution position" as used herein refers to a position on the olefinic compound at which substitution with a boronic acid residue is desired and which is located on a carbon atom which is part of an olefinic carbon to carbon double bond. Each olefinic compound may have more than one double bond and therefore more than 2 vinylic coupling positions.

The term "allylic substitution position" as used herein refers to a position on the olefinic compound at which substitution with a boronic acid residue is desired and which is located on a carbon atom which is directly next to a carbon atom which is part of an olefinic carbon to carbon double bond.

The invention also provides a process for preparing an organic boronic acid derivative comprising reacting diboronic acid with an organic compound having a halogen or halogen-like substituent and an active hydrogen containing substituent in the presence of a Group 8–11 metal catalyst and a suitable base, such that the halogen or halogen-like substituent is substituted with a boronic acid residue.

In another aspect of the invention there is provided a process for preparing an organic boronic acid derivative comprising reacting diboronic acid with an organic compound having a halogen or halogen-like substituent in the presence of a Group 8–11 metal catalyst. and a suitable base in a protic solvent, such that the halogen or halogen-like substituent is substituted with a boronic acid residue.

In another aspect of the invention there is provided a process for preparing an organic boronic acid derivative comprising reacting diboronic acid with an olefinic or acetylenic compound having respectively at least one carbon to carbon double bond or at least one carbon to carbon triple bond and an active hydrogen containing substituent, in the presence of a Group 8–11 metal catalyst, such that a boronic acid residue is introduced on one or two of the carbon atoms of the respective double or triple bonds.

In another aspect of the invention there is provided a process for preparing an organic boronic acid derivative comprising reacting diboronic acid with an olefinic or acetylenic compound having respectively at least one carbon to carbon double bond or at least one carbon to carbon triple bond, in the presence of a Group 8–11 metal catalyst in a protic solvent, such that a boronic acid residue is introduced on one or two of the carbon atoms of the respective double or triple bonds.

In yet another aspect, there is provided a process for preparing an organic boronic acid derivative which comprises reacting an olefinic compound having a leaving group at an allylic substitution position with diboronic acid in the presence of a Group 8–11 metal catalyst, in a protic solvent, such that the leaving group is replaced by a boronic acid residue.

In yet another aspect, there is provided a process for preparing an organic boronic acid derivative which comprises reacting an olefinic compound having a leaving group at an allylic substitution position and an active hydrogen containing substituent with diboronic acid in the presence of a Group 8–11 metal catalyst, such that the leaving group is substituted with a boronic acid residue.

The process according to the present invention provides a route to organic boronic acid derivatives which could not be readily obtainable using conventional processes. Some of these organic boron acid derivatives are novel and represent a further aspect of the present invention.

Tables 1 and 2 below show the structures of some novel and known organic boronic acid derivatives obtainable according to the process of the present invention.

TABLE 1

KNOWN BORONIC ACIDS PREPARED BY DIBORON METHODOLOGY

| Compound Number | COMPOUND STRUCTURE | Calc M/Z | Found M/z |
|---|---|---|---|
| 1 | [structure] | 166 | 165 (Cl⁻) |
| 2 | [structure] | 300 | 299 (Cl⁻) |
| 3 | [structure] | 152 | 151 (Cl⁻) |
| 4 | [structure] | 166 | 165 (Cl⁻) |
| 5 | [structure] | 165 | 164 (Cl⁻) |
| 6 | [structure] | 122 | Confirmed by HPLC |

TABLE 2

NOVEL BORONIC ACIDS PREPARED BY DIBORON METHODOLOGY

| Compound Number | COMPOUND STRUCTURE | Calc M/Z | Found M/z |
|---|---|---|---|
| 7 | [structure] | 302 | 301 (Cl⁻) |

TABLE 2-continued

NOVEL BORONIC ACIDS PREPARED BY DIBORON METHODOLOGY

| Compound Number | COMPOUND STRUCTURE | Calc M/Z | Found M/z |
|---|---|---|---|
| 8 | methyl 3-borono-4-methoxybenzoate structure | 210 | 211 (CI$^+$) |
| 9 | 5-borono-2,3-dihydro-1H-inden-1-one structure | 176 | 177 (CI$^+$) |
| 10 | 4-(2-hydroxyethoxy)phenylboronic acid structure | 182 | 181 (CI$^-$) |
| 11 | 3-phenoxyphenylboronic acid structure | 214 | 213 (CI$^-$) |
| 12 | 4-bromo-3-methylphenylboronic acid and/or 4-bromo-2-methylphenylboronic acid structures | 214 | 213 (CI$^-$) |
| 13 | 4,4-dimethyl-6-oxocyclohex-1-enylboronic acid structure | 168 | Confirmed by HPLC |
| 14 | 4-oxo-2-phenylbutan-2-ylboronic acid structure | 192 | Confirmed by HPLC |

TABLE 2-continued

NOVEL BORONIC ACIDS PREPARED BY DIBORON METHODOLOGY

| Compound Number | COMPOUND STRUCTURE | Calc M/Z | Found M/z |
|---|---|---|---|
| 15 | 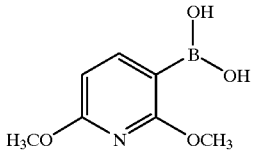 | 183 | 184 (CI⁺) |

| COMPOUND NUMBER | COMPOUND NAME |
|---|---|
| 1 | 1,3-Benzodioxole-5-boronic acid |
| 2 | 1,2,2-Triphenylethyleneboronic acid |
| 3 | 4-Methoxyphenylboronic acid |
| 4 | 4-(2-Hydroxyethyl)phenylboronic acid |
| 5 | 4-(Aminocarbonyl)phenylboronic acid |
| 6 | Phenylboronic acid |
| 7 | 4'-Benzoyl[1,1'-biphenyl]-4-boronic acid |
| 8 | 2-Methoxy-5-(methoxycarbonyl)phenylboronic acid |
| 9 | 1-Oxoindane-5-boronic acid |
| 10 | 4-(2-Hydroxyethoxy)phenylboronic acid |
| 11 | 3-Phenoxyphenylboronic acid |
| 12 | 4-Bromo-3-methylphenylboronic acid |
| 13 | 3,3-Dimethyl-6-oxocyclohexene-1-boronic acid |
| 14 | 3-Oxo-1-phenylbut-1-boronic acid |
| 15 | 2,6-Dimethoxypyridine-3-boronic acid |

Accordingly the present invention provides an organic boronic acid derivative of the formula:

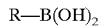

where R is the residue of an organic compound having a substituent reactive with organometallic compounds.

The organic boronic acid derivatives prepared according to the present invention represent a further aspect of the invention and provide suitable intermediates for the coupling of organic compounds via a carbon-carbon bond, or carbon-heteroatom bonds. The organic boronic acid derivatives may also be converted to the corresponding esters or amides by reaction with appropriate alcohols or amines, especially diols and diamines. Surprisingly, it has been found that the presence of appropriate alcohols in the initial stages of the reaction with diboronic acid may be advantageous to the formation of the desired ester product (for example, less dimer formation). Accordingly, performing the reaction in the presence of an appropriate alcohol can give a "one pot" route to organic boronic esters. Furthermore, the use of alcohols can be used to improve the solubility of the diboron reagents in some solvent systems. Preferably the appropriate alcohol is a diol. If the solvent chosen for the reaction is an alcohol or amine it is also possible in some cases to adjust the reaction conditions such that the boronic acid esters/amides are generated in situ.

Accordingly, in another aspect, the present invention provides a process for covalently coupling organic compounds which comprises reacting an organic boronic acid derivative prepared as herein before described with an organic compound having a halogen or halogen-like substituent at a coupling position in the presence of a Group 8–11 metal catalyst and a suitable base.

According to another aspect the present invention provides a "one pot" process for preparing an organic boronic acid ester comprising reacting an organic compound having a boron reactive site with diboronic acid in the presence of a Group 8–11 metal catalyst and an appropriate alcohol under conditions such that the organic boronic acid derivative formed by reaction of diboronic acid with the organic compound, reacts with said appropriate alcohol to form said organic boronic acid ester.

In a further aspect there is provided a "one-pot" procedure for covalently coupling organic compounds comprising reacting:
(i) an organic compound bearing a halogen or halogen-like substituent; or
(ii) an olefinic organic compound; or
(iii) an acetylenic compound
with diboronic acid as hereinbefore defined to form an organic boronic acid derivative, and reacting the organic boronic acid derivative in situ with an organic compound having a halogen or halogen-like substituent at a coupling position in the presence of a Group 8–11 metal catalyst and a suitable base, to form a direct bond between the coupling position and a carbon atom of the organic boronic acid derivative to which the boronic acid residue is attached. This procedure allows the preparation of both symmetrical and unsymmetrical coupled products.

The term "coupling position" as used herein refers to a position on an organic compound at which coupling to another organic compound is desired. Each organic compound may have one or more, preferably between 1 and 6, coupling positions.

The process according to the present invention is applicable to chemistry on solid polymer support or resin bead in the same manner as conventional chemistry is used in combinatorial chemistry and in the preparation of chemical libraries. That is, wherein the organic compound is chemically linked to a solid support. Thus a suitable organic compound having a halogen or halogen-like substituent at a coupling position which is chemically linked to a polymer surface may be reacted with an organic boronic acid derivative intermediate in the presence of a palladium catalyst and a suitable base to form a coupled product linked to the surface of the polymer. Excess reagents and by-products may then be washed away from the surface leaving only the reaction product on the surface. The coupled product may then be isolated by appropriate cleavage of the chemical link from the polymer surface. The process is also possible using the alternative strategy of reacting (i) an organic compound having a halogen or halogen-like substituent, or (ii) an olefinic organic compound, or (iii) an acetylenic compound, linked to a polymer surface with diboronic acid as previously described to form an organic boronic acid derivative chemically linked to the polymer surface. This derivative may then be reacted with an organic compound having a halogen or halogen-like substituent at a coupling position in the presence of a palladium catalyst and a suitable base to prepare the coupled product chemically linked to the polymer. Excess reactants and by-products may be removed by suitable washing and the coupled product may be isolated by chemically cleaving the link to the polymer.

In accordance with the present invention it is also possible to directly functionalise the surface of a polymer, e.g. polystyrene, with a halogen or halogen-like substituent and then convert this functionalised surface to a boronic acid residue surface by reaction of the functionalised polymer with diboronic acid in the presence of a palladium catalyst and a suitable base. The boronic acid residue surface may then be reacted with any suitable organic compound having a halogen or halogen-like substituent. If the organic compound contains other functional groups, for example carboxylic ester, they may be used as linking groups to further extend the chemical reactions applied to the polymer surface.

The term "linking group" as used herein refers to any chain of atoms linking one organic group to another. Examples of linking groups include polymer chains, optionally substituted alkylene group and any other suitable divalent group.

It is also possible to prepare polymers by reaction of organic ring compounds having more than one halogen or halogen-like substituent. Such organic compounds may be reacted with diboronic acid in the presence of a palladium catalyst and a suitable base to form an organic boronic acid derivative having more than one boronic acid residue. These derivatives may be reacted with organic boronic acid derivative or organic compounds having more than one halogen or halogen-like substituent to form a polymer. If the organic compound has three or more halogen or halogen-like substituents which react with the diboronic acid then it is possible to prepare dendritic molecules in accordance with the process of the present invention. It is also possible to form polymers of organic boronic acid derivatives prepared from olefinic organic compounds and acetylenic compounds where there is more than one boronic acid residue.

The organic compounds which are coupled may be separate molecules or may be linked together such that the organic boronic acid derivative formed after reaction with the diboronic acid is able to react at a coupling position located elsewhere in the molecule so as to provide for an intramolecular reaction, such as a ring closure reaction. Similarly the process according to the invention allows intramolecular linking to occur between different regions bearing halogen or halogen-like substituents.

The process according to the invention is also useful for the preparation of reactive intermediates which are capable of taking part in further reactions or rearrangements. These reactive intermediates may be the organic boronic acid derivatives or the coupled products. For example, aryl boronic acid derivatives may take part in one or more of the palladium catalysed reactions of aryl boron compounds described by Miyaura and Suzuki in Chem. Rev. 1995, 95 2457–2483.

The process according to the present invention allows the linking of organic compounds in mild conditions and avoids the use of expensive, difficult to remove and/or toxic reagents and solvents. In this regard boron and boron compounds are generally non-toxic. The reactions may also be performed in relatively cheap solvents such as methanol and ethanol and, in view of the improved control over the reaction steps, it is envisaged that it would be possible to perform the reactions on an industrial scale. The process also allows the linking of organic compounds which contain active hydrogen substituents without the need to protect those substituents during the reaction.

The following Examples are provided to illustrate some preferred embodiments of the invention. However, it is to be understood that the following description is not to supersede the generality of the invention previously described.

EXAMPLES

Preparation 1—Preparation of Diboronic Acid
1 a) Bis(dimethylamino)boron Chloride A 15 liter pilot plant reactor with nitrogen protection from atmospheric moisture was charged with petroleum spirit (b.p .30–40°, 8 l) and cooled to about −60° using an external dry ice/acetone bath. Dimethylamine (2929 g, 64.83 moles) was run into the stirred cold solvent as both liquid and gas and the solution cooled again to −60°. A 10 liter vessel also with nitrogen protection was cooled in a dry ice/acetone bath and similarly charged with petroleum spirit (5 l). Boron trichloride (2000 g, 17.07 moles) was dissolved in the cold solvent, the vessel fitted with a teflon transfer line immersed below the amine solution in the reactor, and the boron trichloride solution slowly pumped across into the dimethylamine solution. There is a huge exotherm with this reaction and great care must be taken to prevent temperature overshoot, and also that the transfer line is not blocked by the amine hydrochloride. The addition was controlled so that the a reaction was maintained at about −20° despite the dry ice cooling bath and addition took place over about 3 hours. The vessel was stirred overnight while it warmed to room temperature.

The stirrer was stopped, the reactor quickly opened, and a teflon tube inserted through the cap fitting and the inner end fitted with a gas distribution tube (pyrex 3830/02M) as filter, and the filter and tube pushed as deeply as possible into the settling amine hydrochloride mass. The reactor was sealed and nitrogen pressure (up to 30 kPa) used to pump the product solution out into a protected receiver. The crystalline amine hydrochloride did not block the small area of the gas tube used as a filter. When all the liquid had been extracted, the filter tube was withdrawn from the solid mass, further petroleum spirit (10l) added to the vessel and the contents cautiously stirred and brought to gentle reflux for 5 mins to extract any remaining product. The filtration and re-extraction process were then repeated a third time, and the combined extracts evaporated on a well-sealed rotary evaporator using liquid feed and nitrogen protection if there was any need to change a receiver or bring the apparatus up to atmospheric pressure. The less volatile residue was then fractionated under reduced pressure and the fraction boiling at 45–48 at 2.5 kPa collected as product (1835 g, 13.65 moles, 70%). Integration of the nmr proton signals at $\delta$ 2.52 [$((CH_3)_2N)_3B$], at $\delta$ 2.71 [$((CH_3)_2N)_2BCl$] and/or at $\delta$ 2.93 [$((CH_3)_2NBCl_2$] was used to determine the composition of the product and whether further dimethylamine or boron trichloride should be added prior the reduction step (below).

b) Tetrakis(dimethylamino)diboron

A 5-liter flange flask reactor in an oil bath with a multi-hole top plate was equipped with an oil-sealed high-shear overhead stirrer, a baffle blade to inhibit "solid-body" stirring, argon gas protection of the contents through a T-piece at the top of a condenser, a thermocouple probe and a 500 ml pressure equalizing dropping funnel. To the flask were added sodium (252 g, 10.95 moles) and xylene (2 l)

and the contents heated from the oil bath to 120°. The stirrer was run up to approx 800 rpm after the sodium had all melted and kept at that speed during the reaction. After the sodium had become a fine grey suspension in the rapidly stirring liquid (about 20 mins), the dropping funnel was charged by pumping through teflon lines under argon pressure, with batches of bis(dimethylamino)boron chloride (total, 1415 g, 10.53 moles). With the reaction mixture at about 125° (gentle xylene reflux), the bis(dimethylamino) boron chloride was slowly added dropwise to the reactor, watching both the thermocouple and the reflux rate: an addition rate of about 500 ml/hour was found satisfactory. The reflux temperature slowly rose as the product concentration increased, and with a mixture temperature of 135° any addition of halide reactant caused an immediate apparent exotherm. The mixture was heated at reflux for a further 1 h after the addition had ceased, then allowed to cool to room temperature (overnight) with the stirrer off.

The supernatant liquid was pumped (argon) into an open pressure vessel attached to a 142 mm pressure filter (Sartorius), the pressure vessel sealed and pressured with argon to 100 kPa The solution of product was filtered into a 5 liter distillation flask with argon protection. The Precipitate in the reaction vessel was washed twice with xylene (500 ml), allowed to settle, and the supernatant similarly filtered. the combined filtrates were fractionated under reduced pressure, initially at 2.5 kPa until all the xylene distilled (b.p. 40–43°), and the pressure gradually reduced to 0.3 kPa when the product distilled. The fraction boiling at 65–67° at 0.3 kPa was collected as pure tetrakis (dimethylamino)diboron (540 g, 2.73 moles, 51.8%).

c) Tetrahydroxydiboron (diboronic acid)

Tetrakis(dimethylamino)diboron (10.64 g, 53.7 mmole) was stirred in ice-cold water (20 ml) in an ice bath and standardized concentrated hydrochloric acid (17.5 ml of 12.78 Molar, 223 mmole. 4.16×diboron reactant) added via a syringe pump over 50 mins to the stirred solution. The mixture was stirred in ice for 15 mins after the addition was complete, the solid filtered off and washed with ice-cold dilute hydrochloric acid (10 ml of 0.064 M) and air dried to give a white solid (3.43 g, 71%).

Ref: McCloskey, A. L., Brotherton, R. J., and Boone, J. L., *J. Amer. Chem. Soc.*, 1961, 83, 4750.

Preparation 2—Larger Scale Preparation of Tetrahydroxydiboron (diboronic acid)

Tetrakis(dimethylamino)diboron (44 g, 0.223 Mole) was stirred in ice-cold water (40 ml) in an ice bath and standardized concentrated hydrochloric acid (73 ml of 12.78 Molar, 0.932 Mole HCl, 4.18×diboron reactant) added via a syringe pump at 50 ml/hr to the stirred solution. The mixture temperature slowly rose to 14°, and cooling was increased by adding ethanol to the ice bath to increase the temperature difference between the reaction mixture and the cooling bath (bath to −10°). The mixture was stirred in the ice bath for 15 mins after the addition was complete, the solid filtered off and washed with ice-cold dilute hydrochloric acid (40 ml of 0.064 M) and air dried to give a white solid (15.47 g, 78%). This material was used without further purification.

Example 1

MeOH as Solvent

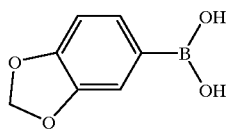

In a Schlenk tube under nitrogen, a mixture of tetrahydroxydiboron (104 mg; 1.16 mmol) [1,1'-bis (diphenylphosphino)ferrocene]dichloropaladium(II) dichloromethane adduct (PdCl$_2$(dppf).CH$_2$Cl$_2$) (26 mg; 0.032 mmol), KOAc (302 mg; 3.08 inmol) and 1-iodo-3,4-methylenedioxybenzene (251 mg; 1.01 mmol) in dry MeOH (5 ml) was sealed and stirred at 40° C. for 3 hours. A small amount of the reaction mixture was added to water, extracted into dichloromethane and then dried over MgSO$_4$. The reaction solution was analysed by HPLC (Waters 600E) under the following conditions: Zorbax ODS, 4.6 mm×25 cm column, λ=230 nm, 2 ml/min using 20% CH$_3$CN:80% H$_2$O to 90% CH$_3$CN:10% H$_2$O over 25 minutes. The major peak at 5.82 mins was identified as 1,3-benzodioxole-5-boronic acid by LC/MS. Addition of authentic 1,3-benzodioxole-5-boronic acid to the reaction solution and analysis by HPLC under the same conditions provided further evidence that the desired aryl boronic acid had formed.

The reaction solution was also analysed under the following conditions: Alltima C18, 5 micron, 4.6 mm×15 cm column, λ=230 nm, 2 ml/min using 20% CH$_3$CN:80% H$_2$O to 100% CH$_3$CN over 15 minutes. The major peak at 3.33 mins was identified as 1,3-benzodioxole-5-boronic acid after the addition of some authentic material to the reaction solution and analysis by HPLC under the same conditions.

Example 2

EtOH as Solvent

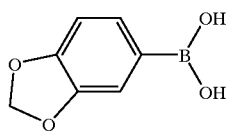

In a Schlenk tube under nitrogen, a mixture of tetrahydroxydiboron (148 mg; 1.65 mmol), PdCl$_2$(dppf).CH$_2$Cl$_2$ (28 mg; 0.035 mmol), KOAc (313 mg; 3.19 mmol) and 1-iodo-3,4-methylenedioxybenzene (252 mg; 1.02 mmol) in dry EtOH (5 ml) was sealed and stirred at 40° C. for 18 hours. A small amount of the reaction mixture was diluted with CH$_3$CN/H$_2$O, filtered through glass fiber filter paper and analysed by HPLC (Waters 600E) under the following conditions: Zorbax ODS, 4.6 mm×25 cm column, λ=230 mn, 2 ml/min using 20% CH$_3$CN:80% H$_2$O to 90% CH$_3$CN:10% H$_2$O over 25 minutes. A major peak was observed at 5.26 minutes. Addition of authentic 1,3-benzodioxole-5-boronic acid to the reaction solution and analysis by HPLC under the same conditions confirmed that the desired aryl boronic acid had formed.

Example 3 i-PrOH as Solvent

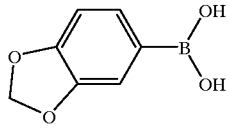

In a Schlenk tube under nitrogen, a mixture of tetrahydroxydiboron (158 mg; 1.76 mmol), $PdCl_2(dppf).CH_2Cl_2$ (26 mg; 0.032 mmol), KOAc (310 mg; 3.16 mmol) and 1-iodo-3,4-methylenedioxybenzene (254 mg; 1.02 mmol) in dry i-PrOH (5 ml) was sealed under nitrogen and stirred at 40° C. for 18 hours. A small amount of the reaction mixture was diluted with $CH_3CN/H_2O$, filtered through glass fiber filter paper and analysed by HPLC (Waters 600E) under the following conditions: Zorbax ODS, 4.6 mm×25 cm column, $\lambda$=230 nm, 2 ml/min using 20% $CH_3CN$:80% $H_2O$ to 90% $CH_3CN$:10% $H_2O$ over 25 minutes. The peak at 6.78 mins was identified as 1,3-benzodioxole-5-boronic acid after addition of authentic material to the reaction solution and analysis by HPLC under the same conditions.

Example 4

DMSO as Solvent

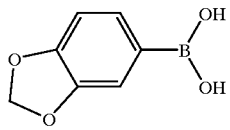

In a Schlenk tube under nitrogen, a mixture of tetrahydroxydiboron (152 mg; 1.70 mmol), $PdCl_2(dppf).CH_2Cl_2$ (27 mg; 0.033 mmol), KOAc (300 mg; 3.06 mmol) and 1-iodo-3,4-methylenedioxybenzene (249 mg; 1.00 mmol) in dry DMSO (5 ml) was sealed and stirred at 40° C. for 18 hours. A small amount of the reaction mixture was diluted with $CH_3CN/H_2O$, filtered through glass fiber filter paper and analysed by HPLC (Waters 600E) under the following conditions: Zorbax ODS, 4.6 mm×25 cm column, $\lambda$=230 nm, 2 ml/min using 20% $CH_3CN$:80% $H_2O$ to 90% $CH_3CN$:10% $H_2O$ over 25 minutes. The major peak at 6.58 mins was identified as 1,3-benzodioxole-5-boronic acid after addition of authentic material to the reaction solution and analysis by HPLC under the same conditions.

Example 5

DMF as Solvent

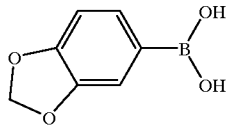

In a Schlenk tube under nitrogen, a mixture of tetrahydroxydiboron (131 mg; 1.46 mmol), $PdCl_2(dppf).CH_2Cl_2$ (27 mg; 0.033 mmol), KOAc (286 mg; 2.91 mmol) and 1-iodo-3,4-methylenedioxybenzene (243 mg; 0.980 mmol) in dry DMF (5 ml) was sealed and stirred at 40° C. for 2.5 days. A small amount of the reaction mixture was diluted with $CH_3CN/H_2O$, filtered through glass fiber filter paper and analysed by HPLC (Waters 600E) under the following conditions: Alitima C18, 5 micron, 4.6 mm×25 cm column, $\lambda$=230 nm, 2 ml/min using 20% $CH_3CN$:80% $H_2O$ to 100% $CH_3CN$ over 15 minutes. The peak at 2.87 mins was identified as 1,3-benzodioxole-5-boronic acid after addition of authentic material to the reaction solution and analysis by HPLC under the same conditions.

Example 6

$H_2O$ as Solvent

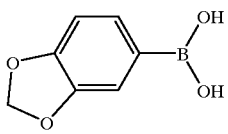

In a Schlenk tube under nitrogen, a mixture of tetrahydroxydiboron (123 mg; 1.37 mmol). $PdCl_2(dppf).CH_2Cl_2$ (23 mg; 0.028 mmol), KOAc (271 mg; 2.76 mmol) and 1-iodo-3,4-methylenedioxybenzene (220 mg; 0.887 mmol) in degassed $H_2O$ (5 ml) was sealed and stirred at 40° C. for 18 hours. A small amount of the reaction mixture was diluted with $CH_3CN/H_2O$, filtered through glass fiber filter paper and analysed by HPLC (Waters 600E) under the following conditions: Alltima C18, 5 micron, 4.6 mm×25 cm column, $\lambda$=230 nm, 2 m/min using 20% $CH_3CN$:80% $H_2O$ to 100% $CH_3CN$ over 15 minutes. The peak at 3.18 mins was identified as 1,3-benzodioxole-5-boronic acid after addition of authentic material to the reaction solution and analysis by HPLC under the same conditions.

FUNCTIONAL GROUP EXAMPLES

Example 7

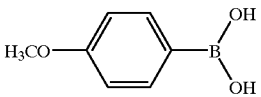

In a Schlenk tube under nitrogen, a mixture of tetrahydroxydiboron (99 mg; 1.10 mmol), $PdCl_2(dppf).CH_2Cl_2$ (26 mg; 0.032 mmol), KOAc (288 mg; 2.93 mmol) and 4-iodoanisole (231 mg; 0.987 mmol) in dry MeOH (5 ml) was sealed under nitrogen and stirred at 40° C. for 18 hours. A small amount of the reaction mixture was added to water, extracted into dichloromethane and then dried over $MgSO_4$. The reaction solution was diluted with $CH_3CN$, filtered through glass fiber filter paper and analysed by HPLC (Waters 600E) under the following conditions: Zorbax ODS, 4.6 mm×25 cm column, $\lambda$=230 nm, 2 ml/min using 20% $CH_3CN$:80% $H_2O$ to 90% $CH_3CN$:10% $H_2O$ over 25 minutes. A major peak (84%) was observed at 6.79 mins which was identified as 4-methoxyphenylboronic acid by LC/MS. Addition of authentic 4-methoxyphenylboronic acid to the reaction solution and analysis by HPLC under the same conditions provided further evidence that the desired arylboronic acid had formed.

Example 8

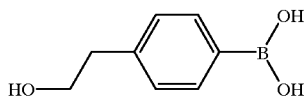

In a Schlenk tube under nitrogen, a mixture of tetrahydroxydiboron (120 mg; 1.34 mmol), PdCl$_2$(dppf).CH$_2$Cl$_2$, (26 mg; 0.032 mmol), KOAc (268 mg; 2.73 mmol) and 4-bromophenylethyl alcohol (177 mg; 0.880 mmol) in dry DMSO (5 ml) was sealed and stirred at 40° C. for 18 hours. A small amount of the reaction mixture was added to water, extracted into dichloromethane and then dried over MgSO$_4$. The reaction solution was diluted with CH$_3$CN, filtered through glass fiber filter paper and analysed by HPLC (Waters 600E) under the following conditions: Zorbax ODS, 4.6 mm×25 cm column, λ=230 nm, 2 ml/min using 20% CH$_3$CN:80% H$_2$O to 90% CH$_3$CN:10% H$_2$O over 25 minutes. The new peak observed at 2.49 mins was identified as the arylboronic acid by LC/MS.

Example 9

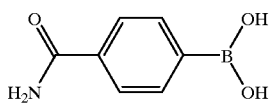

In a Schienk tube under nitrogen, a mixture of tetrahydroxydiboron (126 mg; 1.41 mmol), PdCl$_2$(dppf).CH$_2$Cl$_2$ (24 mg; 0.029 mmol), KOAc (276 mg; 2.81 mmol) and 4-iodobenzamnide (219 mg; 0.886 mmol) in dry DMSO (5 ml) was sealed and stirred at 40° C. for 18 hours. A small amount of the reaction mixture was diluted with CH$_3$CN/H$_2$O, filtered through glass fiber filter paper and analysed by HPLC (Waters 600E) under the following conditions: Zorbax ODS, 4.6 mm×25 cm column, λ=230 nm, 2 ml/min using 20% CH$_3$CN:80 % H$_2$O to 90% CH$_3$CN:10% H$_2$O over 25 minutes. The new peak observed at 2.81 mins was identified as the arylboronic acid by LC/MS.

Example 10

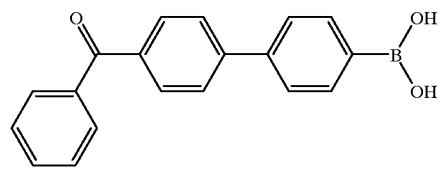

In a Schlenk tube under nitrogen, a mixture of tetrahydroxydiboron (117 mg; 1.31 mmol), PdCl$_2$(dppf).CH$_2$Cl$_2$ (22 mg; 0.027 mmol), KOAc (275 mg; 2.80 mmol) and 4-benzoyl-4'-bromobiphenyl (303 mg; 0.899 mmol) in dry DMSO (5 ml) was sealed under nitrogen and stirred at 40° C. for 18 hours. A small amount of the reaction mixture was diluted with CH$_3$CN/H$_2$O, filtered through glass fiber filter paper and analysed by HPLC (Waters 600F) under the following conditions: Alltima C18, 5 micron, 4.6 mm×15 cm column, λ=230 nm, 2 ml/min using 20% CH$_3$CN:80% H$_2$O to 90% CH$_3$CN:10% H$_2$O over 25 minutes. A major peak was observed at 13.08 mins and identified as the arylboronic acid by LC/MS.

Example 11

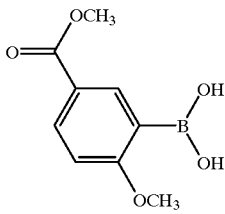

In a Schlenk tube under nitrogen, a mixture of tetrahydroxydiboron (120 mg; 1.34 mmol), PdCl$_2$(dppf).CH$_2$Cl$_2$ (24 mg; 0.029 mmol), KOAc (272 mg; 2.77 mmol) and methyl 3-iodo-4-methoxybenzoate (262 mg; 0.897 mmol) in dry DMSO (5 ml) was sealed and stirred at 40° C. for 18 hours. A small amount of the reaction mixture was diluted with CH$_3$CN/H$_2$O, filtered through glass fiber filter paper and analysed by HPLC (Waters 600E) under the following conditions: Zorbax ODS, 4.6 mm×25 cm column, λ=230 nm, 2 ml/min using 20% CH$_3$CN:80% H$_2$O to 90% CH$_3$CN:10% H$_2$O over 25 minutes. A new peak was observed at 5.65 mins and identified as the desired arylboronic acid by LC/MS.

Example 12

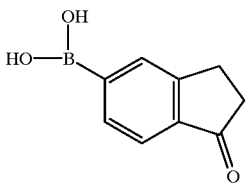

In a Schlenk tube under nitrogen, a mixture of tetrahydroxydiboron (123 mg; 1.37 mmol), PdCl$_2$(dppt).CH$_2$Cl$_2$ (23 mg; 0.028 mmol), KOAc (269 mg; 2.74 mmol) and 5-bromo-1-indanone (187 mg; 0.866 mmol) in dry DMSO (5 ml) was sealed and stirred at 40° C. for 18 hours. A small amount of the reaction mixture was diluted with CH$_3$CN/H$_2$O, filtered through glass fiber filter paper and analysed by HPLC (Waters 600E) under the following conditions: Zorbax ODS, 4.6 mm×25 cm column, λ=230 nm, 2 ml/min using 20% CH$_3$CN:80% H$_2$O to 90% CH$_3$CN:10% H$_2$O over 25 minutes. A new peak was observed at 3.54 mins and identified as the desired arylboronic acid by LC/MS.

Example 13

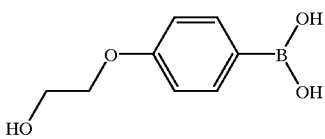

In a Schlenk tube under nitrogen, a mixture of tetrahydroxydiboron (130 mg; 1.45 mmol), PdCl$_2$(dppf).CH$_2$Cl$_2$ (25 mg; 0.031 mmol), KOAc (295 mg; 3.01 mmol) and 2-(4-bromophenoxy)ethanol (214 mg; 0.986 mmol) in dry MeOH (5 ml) was sealed and stirred at 40° C. for 18 hours. A small amount of the reaction mixture was diluted with CH$_3$CN/H$_2$O, filtered through glass fiber filter paper and analysed by HPLC (Waters 600E) under the following conditions: Alltima C18, 5 micron, 4.6 mm×25 cm column, λ=230 nm, 2 ml/min using 20% CH$_3$CN:80% H$_2$O to 100% CH$_3$CN over 15 minutes. A new peak was observed at 1.36 mins and identified as the desired arylboronic acid by LC/MS.

Example 14

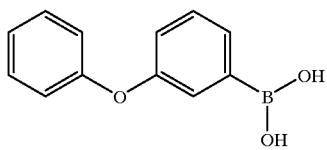

In a Schlenk tube under nitrogen, a mixture of tetrahydroxydiboron (128 mg; 1.43 mmol), PdCl$_2$(dppf).CH$_2$Cl$_2$ (24 mg; 0.029 mmol), KOAc (294 mg; 3.00 mmol) and 5-bromodiphenyl ether (244 mg; 0.983 mmol) in dry MeOH (5 ml) was sealed and stirred at 40° C. for 18 hours. A small amount of the reaction mixture was diluted with CH$_3$CN/H$_2$O, filtered through glass fiber filter paper and analysed by HPLC (Waters 600E) under the following conditions: Alltima C18, 5 micron, 4.6 mm×25 cm column, λ=230 nm, 2 ml/min using 20% CH$_3$CN:80% H$_2$O to 100% CH$_3$CN over 15 minutes. A new peak was observed at 8.65 mins and identified as the arylboronic acid by LC/MS.

Example 15

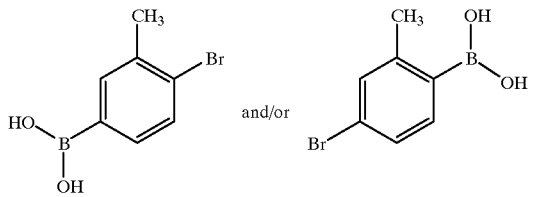

In a Schlenk tube under nitrogen, a mixture of tetrahydroxydiboron (134 mg; 1.49 mmol), PdCl$_2$(dppf).CH$_2$Cl$_2$ (24 mg; 0.029 mmol), KOAc (291 mg; 2.96 mmol) and 2,5-dibromotoluene (244 mg; 0.976 mmol) in dry MeOH (5 ml) was sealed under nitrogen and stirred at 40° C. for 18 hours. A small amount of the reaction mixture was diluted with CH$_3$CN/H$_2$O and filtered through glass fiber filter paper. The desired arylboronic acid detected by LC/MS.

A small amount of the reaction mixture was added to water, extracted into diethyl ether and then dried over MgSO$_4$. Excess pinacol was added to the extract and the solution analysed by GC. A new peak was detected and identified as the corresponding arylborate by GC/MS.

Example 16

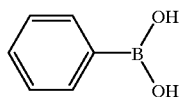

In a Schlenk tube under nitrogen, a mixture of tetrahydroxydiboron (124 mg; 1.38 mmol), PdC$_2$(dppf).CH$_2$Cl$_2$ (24 mg; 0.029 mmol), KOAc (267 mg; 2.72 mmol) and phenyl-trifluoromethanesulfonate (204 mg; 0.902 mmol) in dry MeOH (5 ml) was sealed and stirred at 40° C. for 18 hours. A small amount of the reaction mixture was diluted with CH$_3$CN/H$_2$O, filtered through glass fiber filter paper and analysed by HPLC (Waters 600E) under the following conditions: Alltima C18, 5 micron, 4.6 mm×25 cm column, λ=230 nm, 2 ml/min using 20% CH$_3$CN:80% H$_2$O to 100% CH$_3$CN over 15 minutes. The peak at 1.87 mins was identified as phenylboronic acid after addition of authentic material to the reaction solution and analysis by HPLC under the same conditions.

Example 17

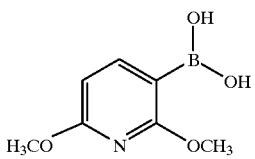

In a dry Schlenk tube fitted with a magnetic stirrer and flushed with argon were placed 3-iodo-2,6-dimethoxypyridine (494 mng, 2 mmoles), tetrahydroxydiboron (177 mg), potassium acetate (326 mg, 3.3 mmoles) and [1,2-bis(diphenylphosphino)-ferrocene] dichloropalladium(II) (57 mg, 0.07 mmoles), followed by dry methanol (10 ml), the flask sealed, shaken, then stirred overnight in an oil bath at 50°. A small amount of the reaction mixture was diluted with CH$_3$CN/H$_2$O and filtered through glass fiber filter paper. 2,6-Dimethoxy-pyridine-3-boronic acid was identified as a product by LC/MS.

ALKENE EXAMPLES

Example 18

MeOH as Solvent

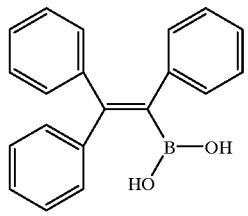

In a Schlenk tube under nitrogen, a mixture of tetrahydroxydiboron (82 mg; 0.91 mmol), PdCl$_2$(dppf).CH$_2$Cl$_2$ (19 mg; 0.023 mmol), KOAc (219 mg; 2.23 mmol) and bromotriphenylethylene (247 mg; 0.737 mmol) in dry MeOH (5 ml) was sealed and stirred at 40° C. for 18 hours. A small amount of the reaction mixture was added to water, extracted into dichloromethane and then dried over MgSO$_4$. The reaction solution was diluted with CH$_3$CN, filtered through glass fiber filter paper and analysed by HPLC (Waters 600E) under the following conditions: Zorbax ODS, 4.6 mm×25 cm column, λ=230 nm, 2 ml/min using 80% CH$_3$CN:20% H$_2$O. The new peak observed at 1.96 mins was identified as 1,2,2-triphenylvinylboronic acid by LC/MS.

The reaction solution was also analysed under the following conditions: Alltima C18, 5 micron, 4.6 mm×15 cm column, λ=230 nm, 2 ml/min using 20% CH$_3$CN:80% H$_2$O to 100% CH$_3$CN over 15 minutes. The 1,2,2-triphenylvinylboronic acid appeared at 9.93 mins under these conditions.

Example 19

DMF as Solvent

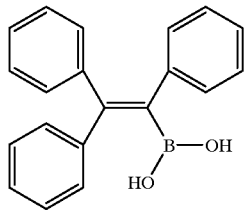

In a Schlenk tube under nitrogen, a mixture of tetrahydroxydiboron (135 mg; 1.51 mmol), $PdCl_2(dppf).CH_2Cl_2$ (26 mg; 0.032 mmol), KOAc (290 mg; 2.95 mmol) and bromotriphenylethylene (323 mg; 0.963 mmol) in dry DMF (5 ml) was sealed and stirred at 40° C. for 2.5 days. A small amount of the reaction mixture was added to water, extracted into dichloromethane and then dried over $MgSO_4$. This reaction solution was diluted with $CH_3CN$ and filtered through glass fiber filter paper. The 1,2,2-triphenylvinylboronic acid was identified by HPLC (Waters 600E) under the following conditions: Alitima C18, 5 micron, 4.6 mm×25 cm column, $\lambda$=230 nm, 2 ml/min using 80% $CH_3CN$:20% $H_2O$ to 100% $CH_3CN$ over 15 minutes.

Example 20

EtOH as Solvent

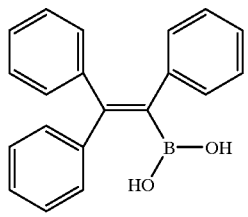

In a Schlenk tube under nitrogen, a mixture of tetrahydroxydiboron (120 mg; 1.33 mmol), $PdCl_2(dppf).CH_2Cl_2$ (23 mg; 0.028 mmol), KOAc (267 mg; 2.72 mmol) and bromotriphenylethylene (295 mg; 0.880 mmol) in dry EtOH (5 ml) was sealed under nitrogen and stirred at 40° C. for 18 hours. A small amount of the reaction mixture was added to water, extracted into dichloromethane and then dried over $MgSO_4$. This reaction solution was diluted with $CH_3CN$ and filtered through glass fiber filter paper. The 1,2,2-triphenylvinylboronic acid was identified by HPLC (Waters 600E) under the following conditions: Alltima C18, 5 micron, 4.6 mm×25 cm column, $\lambda$=230 nm, 2 ml/min using 80% $CH_3CN$:20% $H_2O$ to 100% $CH_3CN$ over 15 minutes.

Example 21 i-PrOH as Solvent

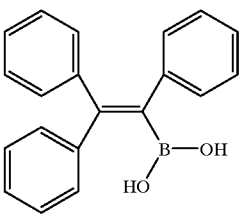

In a Schlenk tube under nitrogen, a mixture of tetrahydroxydiboron (127 mg; 1.42 mmol), $PdCl_2(dppf).CH_2Cl_2$ (22 mg; 0.027 mmol), KOAc (273 mg; 2.78 mmol) and bromotriphenylethylene (296 mg; 0.883 mmol) in dry i-PrOH (5 ml) was sealed and stirred at 40° C. for 18 hours. A sample of the reaction mixture was diluted with $CH_3CN$ and filtered through glass fiber filter paper. The 1,2,2-triphenylvinylboronic acid was identified by HPLC (Waters 600E) under the following conditions: Alltima C18, 5 micron, 4.6 mm×25 cm column, $\lambda$=230 nm, 2 ml/min using 80% $CH_3CN$:20% $H_2O$ to 100% $CH_3CN$ over 15 minutes.

Example 22

$H_2O$ as Solvent

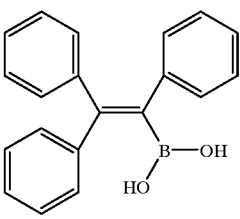

In a Schlenk tube under nitrogen, a mixture of tetrahydroxydiboron (127 mg; 1.42 mmol), $PdCl_2(dppf).CH_2Cl_2$ (25 mg; 0.031 mmol), KOAc (273 mg; 2.78 mmol) and bromotriphenylethylene (296 mg; 0.883 mmol) in degassed $H_2O$ (5 ml) was sealed and stirred at 40° C. for 18 hours. A small amount of the reaction mixture was added to water, extracted into dichloromethane and then dried over $MgSO_4$. This reaction solution was diluted with $CH_3CN$ and filtered through glass fiber filter paper. The 1,2,2-triphenylvinylboronic acid was identified by HPLC (Waters 600E) under the following conditions: Alitima C18, 5 micron, 4.6 mm×25 cm column, $\lambda$=230 nm. 2 ml/min using 80% $CH_3CN$:20% $H_2O$ to 100% $CH_3CN$ over 15 minutes.

Example 23

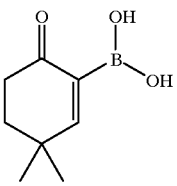

In a Schlenk tube under nitrogen, a mixture of tetrahydroxydiboron (131 mg; 1.46 mmol), $PdCl_2(dppf).CH_2Cl_2$ (26 mg; 0.032 mmol), K₂CO₃ (401 mg; 2.90 mmol) and 4,4-dimethyl-2-iodo-2-cyclohexenone (240 mg; 0.960 mmol) in dry MeOH (5 ml) was sealed and stirred at room temperature (23–25° C.) for 2.5 days. A small amount of the reaction mixture was diluted with MeOH and analysed by GC before adding excess pinacol. GC analysis after the addition of pinacol showed a new peak which was identified as the corresponding vinylborate, thus providing evidence for the formation of the vinylboronic acid initially.

Example 24

Reaction of Enones

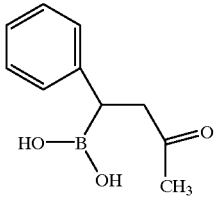

In a Schlenk tube under nitrogen, a solution of tetrahydroxydiboron (121 mg; 1.35 mmol), Pt(PPh₃)₄ (42 mg; 0.034 mmol) and trans-4phenyl-3-buten-2-one (127 mg; 0.869 mmol) in dry DMF (5 ml) was sealed and stirred at 40° C. for 18 hours. A small amount of the reaction mixture was diluted with MeOH and analysed by GC before adding excess pinacol. GC analysis after the addition of pinacol showed a new peak which was identified as the corresponding vinylborate, thus providing evidence for the formation of the vinylboronic acid initially.

Example 25

One Pot Synthesis using One Base

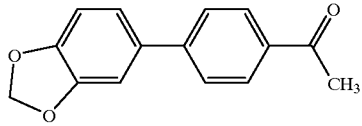

In a Schlenk tube under nitrogen, a mixture of tetrahydroxydiboron (119 mg), PdCl₂(dppf).CH₂Cl₂ (23 mg; 0.028 mmol), K₂CO₃ (389 mg; 2.81 mmol) and 1-iodo-3,4-methylenedioxybenzene (229 mg; 0.923 mmol) in dry MeOH (5 ml) was sealed under nitrogen and stirred at 25° C. After 6 h a small amount of the reaction mixture was added to water, extracted into dichloromethane and then dried over MgSO₄. GC analysis showed the reaction to have gone to completion. Water (1 ml) was added and the reaction mixture was heated at 40° C. for 2.5 h. After cooling to room temperature (23° C.) 4-iodoacetophenone (226 mg; 0.919 mmol) was added and the reaction mixture stirred at room temperature. After 18 h GC analysis showed two major peaks identified as the unsymmetrical biaryl and unreacted 4-iodoacetophenone by GC/MS.

Example 26

Variation of the Catalyst

The reaction solutions in this example were analysed by gc (fid detection) after conversion of the boronic acid species into their pinacolate ester derivatives. This was carried out by reacting approx. 0.3 ml of the reaction solution with pinacol (80–90 mg in 0.25 ml diethyl ether) for 30–60 mins. This solution was then treated with more diethyl ether and extracted 3 times with water and the ether solution (1–1.5 ml) dried with MgSO₄ before injection into the gc or gc/ms. A selection of reaction solutions were also analysed by hplc (neat, filtered reaction solutions were used) and the presence of the aryl boronic acid was confirmed by spiking with an authentic sample.

Formation of

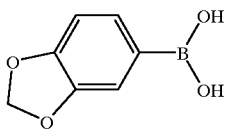

Palladium Catalysts 1. 134 mgs (1.5 mmol) of tetrahydroxydiboron, 26 mg of PdCl₂(dppt). CH₂Cl₂ and 415 mg (3 mmol) K₂CO₃ in a reaction tube under nitrogen were treated with 273 mg (1.10 mmol) 1-iodo-3,4-methylenedioxybenzene in 5 ml dry methanol at 25° C. with stirring. On analysing the reaction solution by gc after 68 h, the 1-iodo-3,4-ethylenedioxybenzene had all been consumed and the required arylboronic acid had formed. This was confirmed by hplc. Some bis(pinacolato)diboron was also observed in the gc indicative that the reaction solution still contained some tetrahydroxydiboron. On the basis of the gc analysis (uncorrected areas) the amount of biaryl formed was small (ratio of 1,3-benzodioxole-5-boronic acid:biaryl was ca. 100:8).

2. 135 mgs (1.5 mmol) of tetrahydroxydiboron, 24 mg of PdCl₂[(C₆H₅)₂PCH₂CH₂P(C₆H₅)₂] and 412 mg (3 mmol) K₂CO₃ in a reaction tube under nitrogen were treated with 244 mg (0.98 mmol) 1-iodo-3,4-methylenedioxybenzene in 5 ml dry methanol at 25° C. with stirring. On analysing the reaction solution by gc after 68 h, some 1-iodo-3,4-methylenedioxybenzene and tetrahydroxydiboron (identified via the bis(pinacolato)diboron derivative) were present in the reaction solution together with some 1,3-benzodioxole-5-boronic acid, identified by hplc and also in the gc as the pinacolate ester. No biaryl was observed but some dehalogenation of the 1-iodo-3,4-methylenedioxybenzene to 1,3-benzodioxole had occurred.

3. 134 mgs (1.5 mmol) of tetrahydroxydiboron, 25 mg of PdCl₂[(C₆H5)₂P(CH₂)₄P(C₆H₅)₂] and 413 mg (3 mmol) K₂CO₃ in a reaction tube under nitrogen were treated with 256 mg (1.03 mmol) 1-iodo-3,4-methylenedioxybenzene in 5 ml dry methanol at 25° C. with stirring. On analysing the reaction solution by gc after 68 h, some 1-iodo-3,4-methylenedioxybenzene and tetrahydroxydiboron (identified via the bis(pinacolato)diboron derivative) were present in the reaction solution. The main product was 1,3-benzodioxole-5-boronic acid, identified by hplc and also in the gc and gc/ms as the pinacolate ester. Some biaryl had formed and some dehalogenation of the 1-iodo-3,4-methylenedioxybenzene to 1,3-benzodioxole was also observed.

4. 134 mgs (1.5 mmol) of tetrahydroxydiboron, 25 mg of PdCl₂[(C₆H₅)₂P(CH₂)₅P(C₆H₅)₂] and 408 mg (3 mmol) K₂CO₃ in a reaction tube under nitrogen were treated with 243 mg (0.98 mmol) 1-iodo-3,4-methylenedioxybenzene in 5 ml dry methanol at 25° C. with stirring. On analysing the reaction solution by gc after 68 h, some 1-iodo-3,4-methylenedioxybenzene and tetrahydroxydiboron (identified via the bis(pinacolato)diboron derivative) were present in the reaction solution. The main product was 1,3-benzodioxole-5-boronic acid, identified directly by hplc and also in the gc and gc/ms as the pinacolate ester. Some biaryl had formed and some dehalogenation of the 1-iodo-3,4-methylenedioxybenzene to 1,3-benzodioxole was also observed.

5. 134 mgs (1.5 mmol) of tetrahydroxydiboron, 52 mg of Pd/C (10% Pd) and 422 mg (3 mmol) $K_2CO_3$ in a reaction tube under nitrogen were treated with 256 mg (1.03 mmol) 1-iodo-3,4-methylenedioxybenzene in 5 ml dry methanol at 25° C. with stirring. On analysing the reaction solution by gc after 18 h, the main product was 1,3-benzodioxole-5-boronic acid, identified as the pinacolate ester derivative, together with the biaryl. Dehalogenation of the 1-iodo-3,4-methylenedioxybenzene to 1,3-benzodioxole was also observed. No iodo or diboron compound was found in the reaction solution.

6. 132 mgs (1.5 mmol) of tetrahydroxydiboron, 27 mg of Pd($CH_3CO$)$_2$ and 420 mg (3 mmol) $K_2CO_3$ in a reaction tube under nitrogen were treated with 250 mg (1.01 mmol) 1-iodo-3,4-methylenedioxybenzene in 5 ml dry methanol at 25° C. with stirring. On analysing the reaction solution by gc after 18 h, the main product was 1,3-benzodioxole-5-boronic acid, identified as the pinacolate ester derivative, together with some biaryl (ratio of 3-benzodioxole-5-boronic acid pinacolate ester derivative to biaryl , uncorrected for fid response, was 3.9:1. Dehalogenation of the 1-iodo-3,4-methylenedioxybenzene to 1,3-benzodioxole was also observed. No iodo or diboron compound was found in the reaction solution.

Platinum Catalyst 134 mgs (1.5 mmol) of tetrahydroxydiboron, 24 mg of $PtCl_2[P(C_6H_5)_3]_2$ and 412 mg (3 mmol) $K_2CO_3$ in a reaction tube under nitrogen were treated with 250 mg (1.01 mmol) 1-iodo-3,4-methylenedioxybenzene in 5 ml dry methanol at 25° C. with stirring. On analysing the reaction solution by gc after 18 h, some 1,3-benzodioxole-5-boronic acid, identified as the pinacolate ester derivative, had formed. No biaryl but 1-iodo-3,4-methylenedioxybenzene and diboron compound were observed by gc in the reaction solution.

Nickel Catalyst 134 mgs (1.5 mmol) of tetrahydroxydiboron, 27 mg of $NiCl_2$(dppf) and 417 mg (3 mmol) $K_2CO_3$ in a reaction tube under nitrogen were treated with 252 mg (1.02 mmol) 1-iodo-3,4-methylenedioxybenzene in 5 ml dry methanol at 25° C. with stirring. On analysing the reaction solution by gc after 18 h, the main product was 1,3-benzodioxole-5-boronic acid, identified as the pinacolate ester derivative. No biaryl had formed. A little diboron compound remained unreacted and some 1,3-benzodioxole was also found in the reaction mixture.

Cobalt Catalyst 135 mgs (1.5 mmol) of tetrahydroxydiboron, 27 mg of $CoCl_2$(dppf) and 284 mg (2 mmol) $K_2CO_3$ in a reaction tube under nitrogen were treated with 261 mg (1.05 mmol) 1-iodo-3,4-methylenedioxybenzene in 5 ml dry methanol at 25° C. with stirring. On analysing the reaction solution by gc after 22 h, some 1,3-benzodioxole-5-boronic acid, identified as the pinacolate ester derivative, had formed. No biaryl but 1-iodo-3,4-methylenedioxybenzene, diboron compound and a little 1,3-benzodioxole were also detected by gc in the reaction solution.

Example 27

Formation of

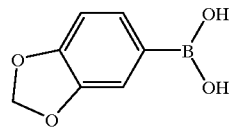

using other bases.

The reaction solutions in this example were analysed by gc (fid detection) after conversion of the boronic acid species into their pinacolate ester derivatives as described in Example 26.

Using, $K_3PO_4$ as Base 136 mgs (1.5 mmol) of tetrahydroxydiboron, 26 mg of $PdCl_2$ (dppf).$CH_2Cl_2$ and 340 mg (1.5 mmol) $K_3PO_4$ in a reaction tube under nitrogen were treated with 259 mg (1.04 mmol) 1-iodo-3,4-methylenedioxybenzene in 5 ml dry methanol at 25° C. for 17 h with stirring. On analysing the reaction solution by gc the main product was found to be 1,3-benzodioxole-5-boronic acid, identified in the gc through its pinacol ester derivative . The only other peaks in the gc, besides starting material, were two peaks both approx. 4% of the area of the main product peak which were assigned by retention time to 1,3-benzodioxole and the biaryl.

Using $C_6H_5OP(O)(ONa)_2.H_2O$ as Base 136 mgs (1.5 mmol) of tetrahydroxydiboron, 25 mg of $PdCl_2$(dppf).$CH_2Cl_2$ and 472 mg (2 mmol) $C_6H_5OP(O)(ONa)_2.H_2O$ in a reaction tube under nitrogen were treated with 249 mg (1.00 mmol) 1-iodo-3,4-methylenedioxybenzene in 5 ml dry methanol for 17 h at 25° C. with stirring. On analysing the reaction solution by gc the main product was found to be 1,3-benzodioxole-5-boronic acid, identified in the gc through its pinacol ester derivative. The amount of biaryl formed was small, its peak area being only 1.5% of that due to the pinacol ester derivative of the 1,3-benzodioxole-5-boronic acid. A small amount of 1,3-benzodioxole was also detected.

Example 28

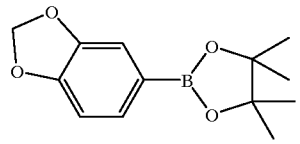

Formation of an ester derivative of an arylboronic acid in a one-pot reaction. 133 mgs (1.5 mmol) of tetrahydroxydiboron, 364 mg (3 mmol) pinacol, 25 mg of $PdCl_2$(dppf). $CH_2Cl_2$ and 283 mg (2 mmol) $K_2CO_3$ in a reaction tube under nitrogen were treated with 249 mg (1.00 mmol) 1-iodo-3,4-methylenedioxybenzene in 5 ml dry methanol for 17 h at 25° C. with stirring. The gc of the reaction solution after extraction into ether and washing with water, contained just 3 peaks with areas of greater than 1% and these were identified by retention times as the required arylboronic acid ester (area 67%), bis(pinacolato)diboron (area 24%) and 1,3-benzodioxole (area 5%). Applying the same gc sample work-up as described in Example 26 (i.e. addition of pinacol), the area of the bis(pinacolato)diboron peak increased to 27% but the 1,3-benzodioxole to arylboronic acid ester peak area ratio remained constant to within experimental error.

Example 29

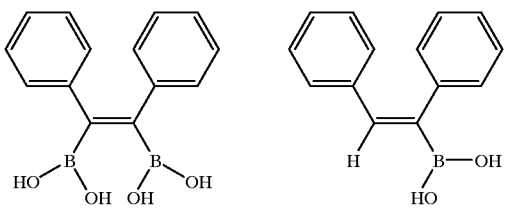

Diboronic acid (tetrahydroxydiboron) (0.135 g; 1.506 mmol), diphenylacetylene (0.196 g; 1.100 mmol) and tetrakis-triphenylphosphine platinum (0.037 g; 0.030 mmol) were placed in a Schlenk tube under an atmosphere of nitrogen. Absolute ethanol (5 mL, dried over 4A molecular sieve) was added under argon, and the tube was heated at 70° C. with stirring for 86 hours. Pinacol was added to convert the boronic acids to their corresponding esters, and gc analysis showed the presence of unreacted diphenylacetylene, monoboronic acid ester and diboronic acid ester, (both identified by gc retention time).

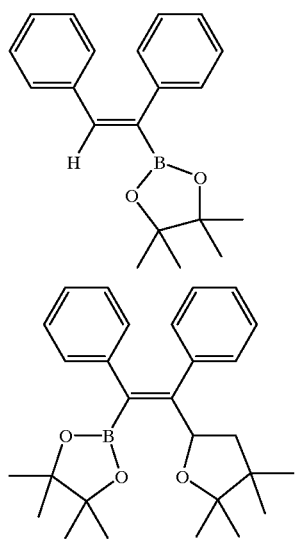

Corresponding reactions were carried out using equivalent amounts of other catalysts, which also resulted in the formation of the mono and diboronic acid compounds (identified by gc). Other catalysts for this reaction include tetrakis(triphenylphosphine)palladium, cis-dichloro bis (triphenylphosphine)plafinum, tris(dibenzylideneacetone) dipalladium, bromo tris(triphenylphosphine)gold, chloro tris (triphenylphosphine)rhodium, dichloro (dppt) palladium and bis(dibenzylideneacetone)platinum.

Example 30

Formation of

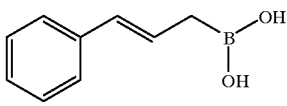

from cinnamyl acetate.

134 mgs (1.5 mmol) of tetrahydroxydiboron and 25 mg of Pd[P(C$_6$H$_5$)$_3$]$_4$ in a reaction tube under nitrogen were treated with 184 mg (1.04 mmol) cinnamnyl acetate in 5 ml dry DMSO for 2 h at 50° C. with stirring. An aliquot of the reaction solution was prepared for gc analysis as described in Example 26. The presence of cinnamyl boronic acid in the reaction solution was confirmed by gc/ms on its pinacol ester derivative.

The reaction can also be carried out in methanol using PdCl$_2$(dppf).CH$_2$Cl$_2$ as catalyst.

135 mgs (1.5 mmol) of tetrahydroxydiboron and 25 mg of PdCl$_2$(dppf).CH$_2$Cl$_2$ in a reaction tube under nitrogen were treated with 178 mg (1.01 mmol) cinnamyl acetate in 5 ml dry methanol for 24 h at 50° C. with stirring. The gc on an aliquot of the reaction solution, prepared for gc analysis as described in Example 26, had only one peak at a retention time longer than that of cinnamyl acetate. The retention time of this peak correspond to that found for the pinacol ester derivative of cinnamyl boronic acid, identified by gc/ms.

Example 31

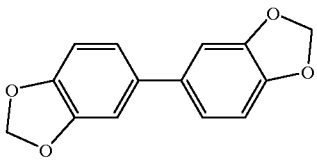

A solution of diboronic acid (0.90 g; 1 mmol), 1-bromo-3,4-(methylenedioxy)benzene (0.400 g; 2 mmol), PdCl$_2$ (dppf).CH$_2$Cl$_2$ (40 g) and Cs$_2$CO$_3$ (1.2 g; 3.7 mmol) in methanol (10 ml) was placed under at atmosphere of nitrogen and heated at 60° C. with stirring. After 2 hrs, gc analysis of the reaction mixture indicated the formation of the product as the major constituent (83%), an intermediate product identified as the aryl boronic acid (7.7%) with the starting 1-bromo-3,4-(methylenedioxy)benzene accounting for the remainder (9.2%).

These examples demonstrate that diboronic acid can be used to synthesise organic boronic acids and that these compounds can be further reacted in situ with the formation of new carbon-carbon bonds.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A process for preparing organic boronic acid derivatives comprising reacting an organic compound having at a substitution position a halogen substituent, or other substituent which undergoes substitution with tetrahydroxydiboron, with tetrahydroxydiboron or its dehydration product in the presence of a Group 8–11 metal catalyst and a suitable base which catalyses, promotes or assists the reaction, such that the halogen or other substituent which undergoes substitution is substituted with a boronic acid residue.

2. A process according to claim 1 wherein the organic compound is aliphatic.

3. A process according to claim 1 wherein the organic compound is olefinic.

4. A process according to claim 3 wherein the halogen or other substituent which undergoes substitution is in a vinylic position.

5. A process according to claim 1 wherein the organic compound is an aromatic compound.

6. A process according to claim 5 wherein the aromatic compound is heterocyclic.

7. A process according to claim 1 herein the Group 8–11 metal catalyst is a palladium, platinum, nickel or cobalt catalyst.

8. A process according to claim 7 wherein the catalyst is a palladium catalyst.

9. A process according to claim 1 wherein the reaction is performed in a protic solvent.

10. A process according to claim 1 wherein the organic compound further includes a substituent selected from the group consisting of hydroxy, amino, imino, acetyleno, carboxy, carboxylato, carboxiimidyl, sulfo, sulfinyl, sulfinimidyl, sulfinohydroximyl, sulfonimidyl, sulfondiimidyl, sulfonohydroximyl, sulfamyl, phosphinyl, phosphinimidyl, phosphonyl, dihydroxyphosphanyl, hydroxyphosphanyl, phosphono, phosphonato, hydrohydroxyphosphoryl, allophanyl, guanidino, hydantoyl, ureido, and ureylene.

11. A process according to claim 1 wherein the suitable base is selected from cyanides and carbonates of Li, Na, K, Rb, Cs, ammonium and the group 2 metals Mg, Ca and Ba, the alkali metal phosphates and the phosphate esters and their alkoxides and phenoxides, thallium hydroxide, alkyl ammonium hydroxides and fluorides.

12. A process according to claim 1 wherein the organic compound is chemically linked to a solid support.

\* \* \* \* \*